(12) United States Patent
Renna et al.

(10) Patent No.: US 9,103,787 B2
(45) Date of Patent: Aug. 11, 2015

(54) OPTICALLY ACCESSIBLE MICROFLUIDIC DIAGNOSTIC DEVICE

(75) Inventors: Lucio Renna, Catania (IT); Clelia Galati, San Gregorio di Catania (IT); Natalia Maria Rita Spinella, Paternè (IT); Salvatore Coffa, Tremestieri Etneo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 369 days.

(21) Appl. No.: 13/111,608

(22) Filed: May 19, 2011

(65) Prior Publication Data

US 2011/0291026 A1    Dec. 1, 2011

(30) Foreign Application Priority Data

May 25, 2010    (IT) ............... TO2010A0437

(51) Int. Cl.
    *G01N 21/00*     (2006.01)
    *G01N 21/64*     (2006.01)
    *B01L 3/00*     (2006.01)

(52) U.S. Cl.
    CPC ...... *G01N 21/6458* (2013.01); *B01L 3/502707* (2013.01); *B01L 3/502715* (2013.01); *G01N 21/6408* (2013.01); *B01L 2300/0636* (2013.01);
    (Continued)

(58) Field of Classification Search
    CPC ............. B01L 3/502707; B01L 3/502715; B01L 2300/0636; B01L 2300/0877; B01L 2300/0887; G01N 21/6408; G01N 21/6458; G01N 2021/6432; G01N 2021/6482
See application file for complete search history.

(56) References Cited

U.S. PATENT DOCUMENTS 5,726,751 A *   3/1998   Altendorf et al. ............. 356/246
6,177,990 B1    1/2001   Kain et al.

(Continued)

FOREIGN PATENT DOCUMENTS

EP    1 295 846 A1    3/2003
WO    WO2010007233    1/2010

OTHER PUBLICATIONS

R. Paganelli et al., Specific IgE antibodies in the diagnosis of atopic disease, Allergy 1998:53:763-768, UK.
Armin Lambacher et al., Fluorescence interference-contrast microscopy on oxidized silicon using a monomolecular dye layer, Applied Physics A 63, 207-216 (1996).
Lung-Wen Tai et al., An automated microfluidic-based immunoassay cartridge for allergen screening and other multiplexed assays, Analytical Biochemistry 391 (2009) 98-105.

(Continued)

*Primary Examiner* — Melanie Y Brown
*Assistant Examiner* — Erik B Crawford
(74) *Attorney, Agent, or Firm* — Seed IP Law Group PLLC

(57) ABSTRACT

A microfluidic diagnostic device (1, 50) comprising a substrate (4); a compatible layer (6) formed on a first face (4a) of the substrate (4); a structural layer (8), formed on top of the compatible layer (6); a channel (10), formed in the structural layer (8) and limited underneath by the compatible layer (6), optically accessible by a first luminous radiation having a first wavelength ($\lambda_e$); and a cover layer (18) made of a material transparent to the first wavelength ($\lambda_e$), arranged on top of the structural layer (8) and sealing the channel (10) at the top, wherein the compatible layer (6) has a thickness equal to approximately a quarter of the first wavelength ($\lambda_e$) divided by the refraction index of the compatible layer (6), or equal to an odd multiple of a quarter of the first wavelength ($\lambda_e$) divided by the refraction index of the compatible layer (6).

13 Claims, 5 Drawing Sheets

(52) U.S. Cl.
CPC .. *B01L 2300/0877* (2013.01); *B01L 2300/0887* (2013.01); *G01N 2021/6432* (2013.01); *G01N 2021/6482* (2013.01)

(56) References Cited

U.S. PATENT DOCUMENTS

| | | | |
|---|---|---|---|
| 2002/0108860 A1* | 8/2002 | Staats | 204/601 |
| 2002/0177135 A1* | 11/2002 | Doung et al. | 435/6 |
| 2004/0086424 A1* | 5/2004 | Schembri | 422/58 |
| 2004/0253545 A1 | 12/2004 | David | |
| 2005/0136685 A1 | 6/2005 | Takenaka et al. | |
| 2005/0176037 A1* | 8/2005 | Mastromatteo et al. | 435/6 |
| 2005/0233440 A1 | 10/2005 | Scurati et al. | |
| 2007/0031287 A1 | 2/2007 | Webster et al. | |
| 2007/0087353 A1 | 4/2007 | Cheng et al. | |
| 2009/0111207 A1 | 4/2009 | Choumane | |
| 2009/0318303 A1 | 12/2009 | Delamarche et al. | |

OTHER PUBLICATIONS

Yann Marcy et al., Innovative integrated system for real-time measurement of hybridization and melting on standard format microarrays, BioTechniques, vol. 44, No. 7, 913-920 (2008).

Marina Cretich et al., High Sensitivity Protein Assays on Microarray Silicon Slides, Analytical Chemistry, vol. 81, No. 13, 5197-5203, (2009).

Shifeng Li et al., Disposable polydimethylsiloxane/silicon hybrid chips for protein detection, Biosensors and Bioelectronics 21, 574-580 (2005).

Cheng-Wey Wei et al., Using a microfluidic device for 1 μl DNA microarray hybridization in 500 s, Nucleic Acids Research, 2005, vol. 33, No. 8 e78.

Regis Peytavi, Microfluidic Device for Rapid (<15 min) Automated Microarray Hybridization, Clinical Chemistry 51:10: 1836-1844 (2005).

* cited by examiner

OPTICALLY ACCESSIBLE MICROFLUIDIC DIAGNOSTIC DEVICE

PRIOR RELATED APPLICATIONS

This invention claims priority to Italian Patent Application No. TO2010A 000437 filed on May 25, 2010 in the name of STMicroelectronics S.r.l.

FEDERALLY SPONSORED RESEARCH STATEMENT

Not applicable.

REFERENCE TO MICROFICHE APPENDIX

Not applicable.

FIELD OF THE INVENTION

The present invention relates to an optically accessible microfluidic device, to a method for manufacture thereof, and to a system that uses the microfluidic diagnostic device.

BACKGROUND OF THE INVENTION

The present invention relates to an optically accessible microfluidic device, to a method for manufacture thereof, and to a system that uses the microfluidic diagnostic device.

As is known, devices of a micromechanical or microelectromechanical (MEMS) type are widely used in industry, medicine and research. MEMS devices offer the advantages of improving the reliability of the assay, reducing sample volumes, as well as reducing the time required for said activities, thus reducing the corresponding costs and improving efficiencies.

Diagnostic devices of a known type basically comprise a solid substrate, generally of a flat type, on which particular receptors, such as, for example, biomolecules (DNA, RNA, proteins, antigens, antibodies, haptens, sugars etc.) or chemicals, or microorganisms or parts thereof (bacteria, viruses, spores, cells, organelles, etc.) are grafted.

By "receptor" what is meant herein is any member of a binding pair or multiple, such that the receptor will bind to or react with, and thus detect, its binding partner(s). Thus, receptor includes traditional receptors such as protein receptor and ligand, but also any member of a binding or interacting multiple such as lectin, carbohydrates, streptavidin, biotin, protein, substrate, oligonucleotides, nucleic acid, porphyrins, metal ions, antibodies, antigens, and the like.

When these receptors come in direct contact with a sample to be analysed, the presence in said sample of molecules capable of binding or interacting with the receptor is detected in some way. For example, binding can be detected with fluorescent or phosphorescent labels, which, when excited with light radiation at a certain wavelength $\lambda_e$, emit a light radiation having a wavelength $\lambda_f$ different from the wavelength $\lambda_e$.

Known fluorescence diagnostic devices comprise a compatible layer, the surface of which is functionalized in such a way as to present sensing areas comprising receptors provided with specific labels. The labels are activated (i.e., they emit a light at a wavelength $\lambda_f$) only when sample of molecules bind or interact with the receptors.

There are many different ways to set up tests involving optical signals. For example, a common three component binding assay uses a first antibody bound to a solid substrate which can bind to an antigen present in a sample solution. Antigen binding is then detected with a second antibody that binds to a different epitope of the same antigen and which has a fluorescent label attached thereto. Thus, the amount of fluorescence detected correlates with the amount of antigen in the sample.

Another example involves binding an oligonucleotide probe to the substrate (or free in solution), which then hybridizes to complementary DNA or cDNA or mRNA in the sample, and the double stranded nucleic acid can be detected with an intercalating dye, such as ethidium bromide, which fluoresces on exposure to UV light.

In yet another example, two fluorescent markers are brought in close proximity in the assay, and quenching of one marker is measured in fluorescence resonance energy transfer (FRET) based assays. The reverse is also possible, that is where the assay separates two labels allowing an increase in signal.

As yet another example, heavy metal binding to fluorophores can also be detected with fluorescent dyes. Regardless of the assay particulars, similar devices can generally be employed with optical assays.

The light radiation in assays such as these can then be collected by an appropriate detector, such as, for example, a photo-detector of a charge-coupled device (CCD) type or of a CMOS type, compatible with the wavelength $\lambda_f$ of the emitted light radiation. The variation of light intensity is a function of the amount of specific labels activated or detected in the assay, and hence of the amount of target in the sample.

The aim of the present invention is to provide an optically accessible microfluidic diagnostic device, a method for manufacture thereof, and a diagnostic system that uses the microfluidic diagnostic device.

By "diagnostic" device herein, we do not imply that the device is used only for medical purposes, but rather a general purpose device that can diagnose the presence (or absence) or concentration of a particular analyte is intended.

SUMMARY OF THE INVENTION

According to the present invention an optically accessible microfluidic diagnostic device, a method for manufacture thereof, and a diagnostic system that uses the microfluidic diagnostic device are provided.

For a better understanding of the present invention, a preferred embodiment thereof is now described, purely by way of non-limiting example, with reference to the attached drawings, wherein:

DESCRIPTION OF EMBODIMENTS OF THE INVENTION

Figure 1:
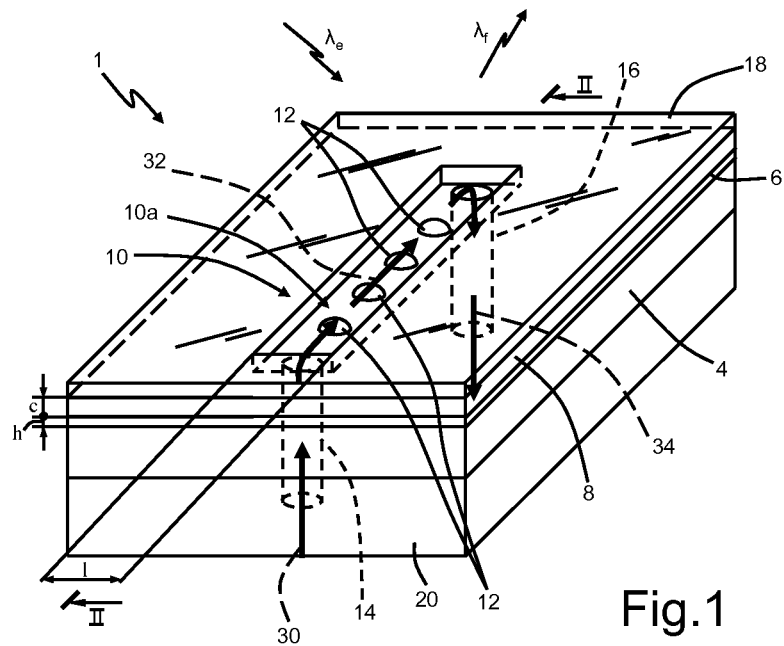
FIG. 1 shows a perspective view of a diagnostic device according to one embodiment of the present invention.

FIG. 1 shows a perspective view of a diagnostic device 1 according to the present invention, in particular a device of a MEMS type designed to be used in fluorescence-detection systems (such as, for example, the system shown in FIG. 11 and described hereinafter with reference to said figure).

The diagnostic device 1 comprises a substrate 4 made of semiconductor material, for example silicon, and a compatible layer 6 arranged on top of, and in direct contact with, the substrate 4. Other suitable substrate materials include metal, or plastic covered by a layer of metal (such as Al, Au, Ag, Pt, etc.), and the like.

The compatible layer 6 is in preferred embodiments a biocompatible layer made of, for example, silicon oxide ($SiO_2$). Other suitable compatible layers include, glass, plastic, and the like.

In the alternative, a non-biocompatible layer can be used and then passivated if needed for the application at issue. It is well known in the art to coat a surface so as to prevent the surface from interfering with the assay. Common passivation materials include silane, albumin, sonnicated salmon sperm DNA, random hexamer oligonucleotides, and the like. With the use of passivating coatings, other substrate materials can be used, such as metals, alloys, ceramics, and the like.

Further, in some applications it may be necessary to functionalize one or more surfaces for the attachment of receptors, e.g., by adding hydroxyl groups (OH groups). Herein, all such surfaces are referred to as "compatible," by which is meant the surface is compatible with the assay and receptors to be used in the device.

The thickness of the substrate 4 can be variable and chosen so as to balance both ease and cost of production and resistance to breakage on impact or stress. Furthermore, the thickness can be decreased if a substantial support underlies the substrate 4, e.g., support 20 in FIG. 1.

The thickness $\underline{h}$ of the compatible layer 6 can be optimized according to the application of the diagnostic device 1. In particular, according to one embodiment of the present invention, the optical thickness of the compatible layer 6 is chosen in such a way that it is equal to approximately ¼ of the wavelength $\lambda_e$ of the excitation light radiation. For instance, the optical thickness can have a value between ¼ $\lambda_e$−20% and ¼ $\lambda_e$+20%.

In practice, in order to obtain a compatible layer 6 having optical thickness $\lambda_e/4$, the refraction index $\underline{n}$ of the material of which the compatible layer 6 is made should be considered. The effective thickness $\underline{h}$ of the compatible layer 6 is hence preferably chosen of between $\lambda_e/(4 \cdot n)$−20% and $\lambda_e/(4 \cdot n)$+20%, preferably equal to $\lambda_e/(4 \cdot n)$.

Using, for example, an excitation radiation having a wavelength $\lambda_e$ in the visible range (for example approximately 400 nm, typically used in Laser Induced Fluorescence technology, or LIF), taking into account the refraction index $\underline{n}$ of the material of which the compatible layer 6 is made (in the case of silicon oxide, said value is approximately n=1.45), the thickness $\underline{h}$ of the compatible layer 6 is chosen equal to 400/(4·1.45) nm, i.e., approximately 68.9 nm, or about 68-70 nm.

For incidence angles of the incident light radiation that are approximately orthogonal with respect to the surface of the compatible layer 6, the choice of the thickness $\underline{h}=\lambda_e/(4 \cdot n)$ determines a maximization of the excitation of the fluorescent labels and, as a consequence, of the light radiation emitted by the excited labels. This is due to constructive interference between the incident light radiation and the portion of the light radiation reflected by the surface of the compatible layer 6.

According to a further embodiment of the present invention, the thickness h of the compatible layer 6 is chosen equal to $\underline{h}=X(\lambda_e/(4 \cdot n))$, where X is an odd number chosen arbitrarily. For values of thickness h that are odd multiples of $\lambda_e/(4 \cdot n)$ there is obtained an effect of gain and maximization of the excitation, analogous to what has been described previously.

In fact, in this way, the portion of the light radiation reflected at the interface between the substrate 4 and the compatible layer 6 combines constructively with the portion of the light radiation reflected superficially by the compatible layer 6. In other words, the bounced light combines with the incident light. This provides a maximization of excitation light and therefore a maximization of signal.

It is evident that in order to take advantage of bounced light contributions to excitation and emitted light, the compatible layer 6 should be made of a material that is transparent to the wavelength $\lambda_e$ of the excitation light radiation and is moreover transparent to the wavelength $\lambda_f$ of the light radiation emitted by the excited labels.

The diagnostic device 1 further comprises a structural layer 8 on top of, and in direct contact with, the compatible layer 6. The structural layer 8 has one or more channels 10 (only one channel 10 is shown in FIG. 1) obtained by removing selectively portions of the structural layer 8 until the compatible layer 6 is reached and exposed.

In the case where a number of channels 10 are present on one and the same diagnostic device, each channel 10 is isolated from other channels 10 by means of the structural layer 8. Thus, the bottom of the channel comprises a biocompatible or compatible layer, and the side walls of the channel are provided by structural layer 8.

FIG. 1 shows by way of example a channel 10 provided with a bottom surface 10a having, in top plan view, a rectangular shape, and being isolated on all four sides by the structural layer 8. Other shapes, different from the rectangular shape, are possible, for example circular, serpentine, or in general polygonal shape, with or without rounded corners are also possible.

The structural layer 8 is preferably made of photoresist. A photoresist that can be used is a base of acrylic polymers, which possess good characteristics of adhesion and strength. The use of a photoresist affords the possibility of forming channels 10 having lateral dimensions (width $\underline{l}$) and vertical dimensions (thickness $\underline{c}$) that can be easily controlled during the manufacturing steps.

Each channel 10 has a shape and dimensions chosen according to the needs presented by the application or use of the device. FIG. 1 shows, not in scale, a channel 10 having the shape of a rectangular strip with a width $\underline{l}$ of between 1 µm and 10000 µm, preferably 200 µm, and a thickness $\underline{c}$ of between 1 µm and 1000 µm, preferably 10 µm.

The channel 10 contains one or more detection regions 12 (for example, in the form of "spots" arranged in series along the channel 10 and separated from one another by approximately 100 µm), comprising receptor biomolecules deposited onto compatible surface 6 in a known way.

For instance, it is possible to use an automated spotting technique, which substantially envisages the use of a mechanical arm that picks up the biological material to be deposited (in liquid solution) and, with micrometric precision, deposits drops of said biological material into the channel 10 to form the detection regions 12.

Typically, each of said drops is of a few picoliters, but drops can be as large as 1-5 µl, or larger, depending on the application and available samples sizes. In the alternative, the entire surface of a given region can be coated if desired for the application at issue.

In addition, the diagnostic device 1 comprises an inlet hole 14 and an outlet hole 16, which are formed through the substrate 4 and the compatible layer 6 and are designed to form, respectively, an access path (see arrow 30) from outside of the diagnostic device 1 towards the channel 10, and an outlet path (see arrow 34) from the channel 10 towards the outside of the diagnostic device 1, through the optional support 20.

The diagnostic device 1 further comprises a cover layer 18, set on top of, and in contact with, the structural layer 8 so as to seal the channel 10 hermetically at the top. In this way, the individual points of access to the channel 10 are the inlet hole 14 and the outlet hole 16. The cover layer 18 is made of a material substantially transparent to light (or, in any case, substantially transparent at the wavelength $\lambda_e$ of the light radiation used for exciting the specific markers and transparent at the wavelength $\lambda_f$ of the light radiation emitted by the excited labels).

In this way, the channel 10 is completely optically accessible from outside the diagnostic device 1. For instance, the cover layer 18 can be an adhesive tape or an adhesive film, or a layer of a material rendered adhesive and arranged on top of the channel 10 so as to seal it.

The cover layer 18 can be made of a compatible transparent polymeric material, in particular bio-compatible, for example, chosen in the group comprising polyethylene, glass, Plexiglas, polycarbonate, polydimethylsiloxane (PDMS), and the like.

In general, it is important for the step of covering of the channel to avoid damaging the material or receptor deposited in the channel 10, and hence any process that envisages, for example, thermal treatments at a high temperature or using plasma, should be avoided for heat sensitive molecules.

Figure 2:
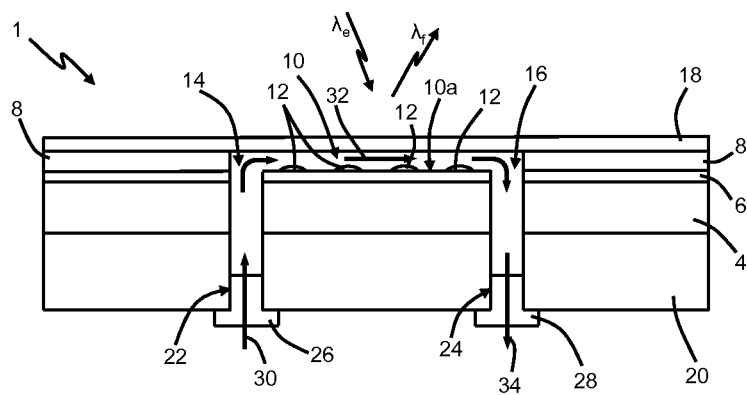
FIG. 2 shows a cross-sectional view of the device of FIG. 1 taken along the line II-II.

FIG. 2 shows a cross-sectional view, taken along the line II-II, of the diagnostic device 1. With joint reference to FIGS. 1 and 2, the diagnostic device 1 further comprises a support 20 made of metal or plastic or ceramic or glass or polymeric material, arranged on the substrate 4 on the free side thereof (opposite to the side adjacent to the compatible layer 6). Support layer may be optional where substrate 4 is thick enough to provide the needed strength and durability.

The support 20 moreover has a first through hole 22 and a second through hole 24, which are formed in areas corresponding to the respective inlet hole 14 and outlet hole 16, for enabling bi-directional fluidic communication between the channel 10 and the outside of the diagnostic device 1. The through holes 22 and 24 can be provided with a respective closing element 26, 28 (shown only in FIG. 2), for example, a plug made of plastic or elastomeric material, which seals the channel 10. The through holes 22, 24 can also be provided with a fast-coupling system for fluidic connections, of a known type, for example, threaded couplings or clamps.

The detection regions 12 comprise, a given type of receptors, such as, for example, biomolecules (DNA, RNA, proteins, antigens, antibodies, etc.) or micro-organisms or parts thereof (bacteria, viruses, spores, cells, organelles, etc.) or any chemicals used for detecting an analyte.

The receptors, provided with specific labels, for example fluorescent labels, are grafted to the bottom surface 10a of the channel 10 by drying or by covalent binding to the surface or to reactive groups placed on the surface. Alternatively, a third member of a binding trio can be provided with the label or labels can be free in solution, and only bind to the binding pair (e.g., EtBr).

In alternative embodiments, the receptors may be free in solution, rather than attached to the device, depending on the application for which the device is to be employed. However, solid phase assays are generally preferred because they allow the opportunity of washing away unbound materials and thus increasing the sensitivity and simplicity of detection assays.

When these receptors are placed in direct contact with a biological or other sample to be analysed comprising molecules able to combine with the receptors, the combination of the molecules with the receptors activates the specific markers. When the markers are activated, they are able to emit autonomously light radiation, or else they may be induced into a state of light emission by means of external excitation. Only the activated markers are able to emit light radiation of their own, whilst non-activated markers do not respond to the external excitation (or in any case, in general, do not emit light radiation or emit light of a different wavelength).

For instance, by functionalizing the detection regions 12 of the compatible layer 6 using IgG, in the presence of a biological liquid introduced (see arrow 30) via the inlet hole 14 into the channel 10 and containing molecules of anti-IgG marked with Cy3, it is possible to detect activated markers by illuminating the detection regions 12 with an excitation light radiation having a wavelength $\lambda_e$=543 nm and by detecting an emitted light radiation having a wavelength $\lambda_f$=570 nm. As has been said, a compatible layer 6 having a thickness $\underline{h}=\lambda_e/(4\cdot n)$ enables maximization of the excitation of the activated labels.

The biological liquid or other sample is made to flow (see arrow 32) along the entire channel 10 in such a way that the biological liquid comes into contact with the detection regions 12 and is then made to exit from the channel 10 via the outlet hole 16 (see arrow 34). The detection of the fluorescence can be made with the channel 10 emptied, not emptied, or only partially emptied, as desired for the application being pursued.

Reading of the emitted light radiation can be carried out by means of a confocal microscope, focused on the bottom surface 10a of the channel 10, preferably with a depth resolution of less than 1 µm. With such a value of depth resolution, the fluorescence detected is principally due to activated markers (and not to phenomena of noise), which indicates that a bond has been made between the receptors set in the channel 10 and target molecules present in the biological liquid or other sample that flows in the channel 10.

With reference to FIGS. 3-9, a method is illustrated for manufacturing the diagnostic device 1 of FIGS. 1 and 2.

In the first place (FIG. 3), the substrate 4 of semiconductor material, for example, silicon, is provided. Then, the compatible layer 6, for example, made of silicon oxide ($SiO_2$) is formed on a first face 4a of the substrate 4. The compatible layer 6 of silicon-oxide can be thermally grown, in a dry or wet environment. This step allows the formation of a compatible layer 6 having a nearly atomically flat surface.

Alternatively, the silicon-oxide layer can be deposited by sputtering or plasma techniques. It is evident that the compatible layer 6 can be obtained with other materials other than silicon oxide, for example, deposited polymeric layers, transparent plastic substrates, or oxynitride, or be passivated after formation, or functionalized for attachment (grafting) of receptors, and the like, as discussed above.

The thickness h of the compatible layer 6, as has been said, depends upon the specific application of the diagnostic device 1 and is preferably $\underline{h}=\lambda_e/(4\cdot n)$. The thermal growth of the silicon oxide enables precisely controlled oxide thicknesses (of the order of fractions of nanometers) to be obtained. However, it is also possible to measure said thickness and reduce it (if the thickness is excessive) by means of chemical-mechanical polishing (CMP) or else continue the process of growth (if the thickness is still insufficient).

Then (FIG. 4), formed on top of the compatible layer 6 is a photoresist layer 8', preferably made of a photoresist of a dry type formed by lamination. Alternatively, the photoresist layer 8' can be formed by spinning of a photoresist of a liquid type.

Figure 4:
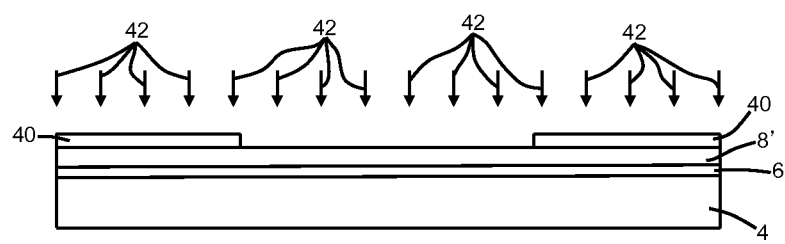
Figure 5:
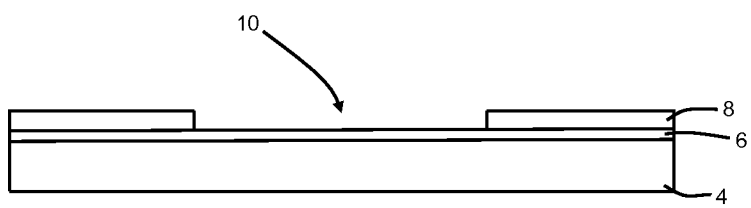
Figure 6:
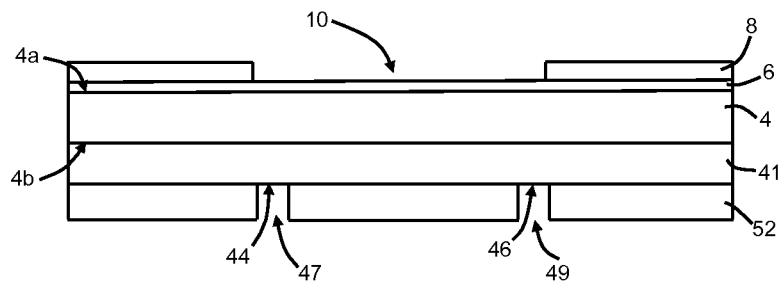

A photolithographic process is then carried out (identified by the arrows 42 in FIG. 4). A mask 40, defining (in a positive or negative way, according to the photoresist used for forming the layer 8') the channel 10 (or a plurality of channels 10 if present) is used for the photolithographic step.

A subsequent etching step enables removal of selective portions of the photoresist layer 8' (the portions exposed to photolithography in the case of positive photoresist or the masked portions in the case of negative photoresist), thus forming (FIG. 5) the structural layer 8 and the channel 10.

Then (FIG. 6), formed on a second face 4b opposite to the first face 4a of the substrate 4 is a backside layer 41 designed to become the supporting layer 20 of FIGS. 1 and 2. The backside layer 41 can, for example, be made of deposited aluminium, of deposited polymeric material, or of plastic material bonded to the second face 4b of the substrate 4.

Then, the inlet hole 14 and outlet hole 16 are formed. For this purpose, a mask 52 is formed on the backside layer 41. The mask 52 is shaped so as to define regions 44 and 46 in which the inlet hole 14 and outlet hole 16 are to be formed (in FIG. 6 said regions 44 and 46 correspond to the surface portions of the layer 41 left uncovered by the mask 52).

Figure 7:
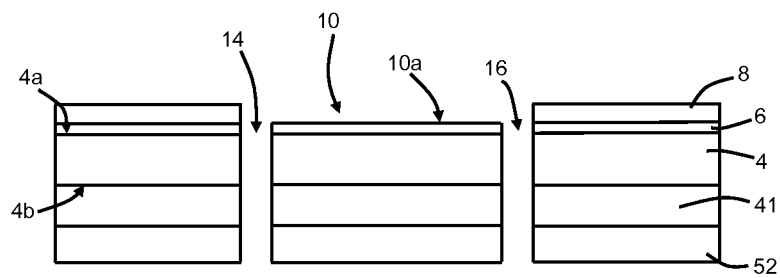
Figure 8:
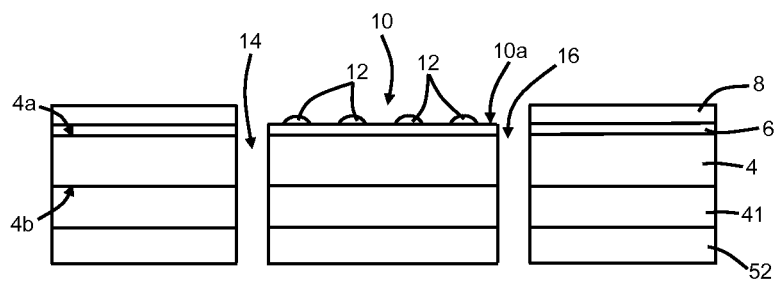
Figure 9:
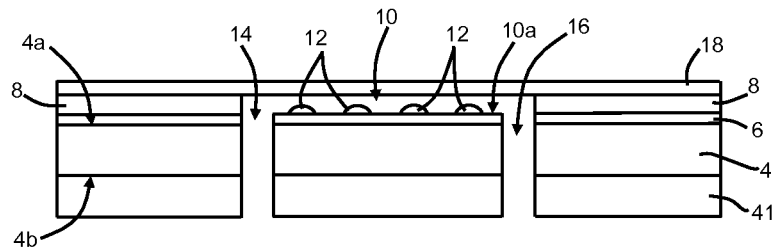

Next, FIG. 7, by means of successive etching steps, the portions of the layer 41 left uncovered by the mask 52 are removed, until the substrate 4 is reached, to form a first hole 47 and a second hole 49 (which, at the end of the manufacturing process, will become the first through hole 22 and the second through hole 24).

Then, by means of a subsequent etching steps or drilling (depending on the material), portions of the substrate 4 accessible via the first and second holes 47, 49 are removed until the compatible layer 6 is reached. Once the compatible layer 6 has been reached, portions thereof not protected by the substrate 4 and/or by the layer 41 are removed, until the channel 10 is reached, thus forming the inlet hole 14 and the outlet hole 16.

According to the materials used for the substrate 4 and for the compatible layer 6 and to the chemical agents used for the etching step, the portions of the substrate 4 and of the compatible layer 6 to be removed can be etched using just one chemical agent (hence in a single etching step) or using different chemical agents (hence in two successive etching steps), or can be etched with a laser depending on the materials used. In addition, the etch may be either a dry type or a wet type etch, as desired.

In the case of a substrate 4 made of silicon and a compatible layer 6 made of silicon oxide, the etch for forming the inlet hole 14 and outlet hole 16 can be a plasma etch, which uses, alternatively, $SF_6$, $CF_4$, or a combination of $SF_6$ and $C_4F_8$. The step of formation of the holes is preferably compatible with the through-silicon via (TSV) technology, which enables removal in a single etching step both of portions of the substrate 4 and of portions of the compatible layer 6.

Then (FIG. 8), a step of cleaning of the bottom surface 10a of the channel 10 is carried out if needed for the application and materials used. For example, the channel 10 can be cleaned using a piranha solution, i.e., a mixture of sulphuric acid $H_2SO_4$ and hydrogen peroxide $H_2O_2$, or alternatively a washing with RCA-1 (sometimes called standard clean SC-1), i.e., a mixture of $H_2O$, $NH_4OH$, $H_2O_2$, which can be followed by a further cleaning with a second washing using a mixture of $H_2O_2$, HCl and $H_2O$. Alternatively, a supercritical liquid $CO_2$ wash can be performed. Many other cleaning methods are known and can be used as needed.

Then, where needed steps of activation (e.g., to expose OH groups) of the bottom surface 10a of the channel 10 are carried out by means of a mixture of HCl and $CH_3OH$, and then a step of functionalization of the bottom surface 10a of the channel 10 is carried out. For example, in the case where the compatible layer 6 is made of silicon oxide, a silanization step is used.

Then, the detection regions 12 are formed, for example using an automatic spotting technique. Advantageously, since the bottom surface 10a of the channel 10 is completely accessible from the top, the step of spotting does not require complex alignment methodologies. Since this step is of a known type, it is not further described herein.

Finally (FIG. 9), the mask 52 is removed, and the cover layer 18 is set on top of the channel 10, in contact with the structural layer 8. The cover layer 18 is, for example, as has been said, an adhesive tape or film, made of compatible, in particular biocompatible, transparent polymeric material. The cover layer 18 may also be of glass.

In alternative embodiments, where a deeper channel is used, the cover layer 18 need not be compatible with the assay, if for example, the sample is not intended to contact the cover. In yet other embodiments, the cover layer 18 may be omitted, e.g., where sample evaporation is not expected to be a problem.

The process described with reference to FIGS. 3-9 can be implemented at an industrial level by processing an entire wafer of semiconductor material, provided on which are a plurality of diagnostic devices 1 of the type described. In this case, at the end of the production steps, the wafer is diced into individual chips (each chip comprising one or more diagnostic devices 1), and packaging of the chips is carried out. Appropriate closing elements 26, 28 (e.g., silicon rubber plugs) can be used for sealing the inlet and outlet holes 14, 16 to obtain the diagnostic device of FIG. 2.

Figure 10:
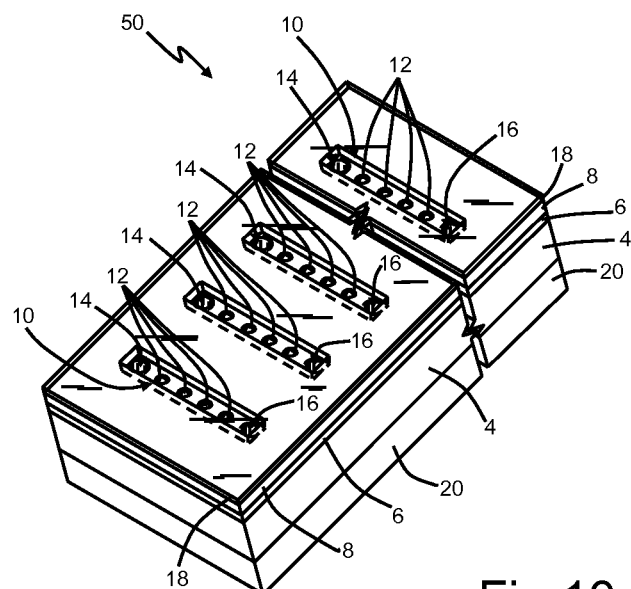
FIG. 10 shows a perspective view of a diagnostic device according to a further embodiment of the present invention.

FIG. 10 shows a diagnostic device 50 provided with a plurality of channels 10, isolated from one another by the structural layer 8 and each provided with an inlet hole 14 and an outlet hole 16. Each channel 10 can be functionalized in a way different from other channels 10 present on the diagnostic device 50. In this way, a single diagnostic device 50 can be used for conducting a plurality of biological analyses.

Figure 11:
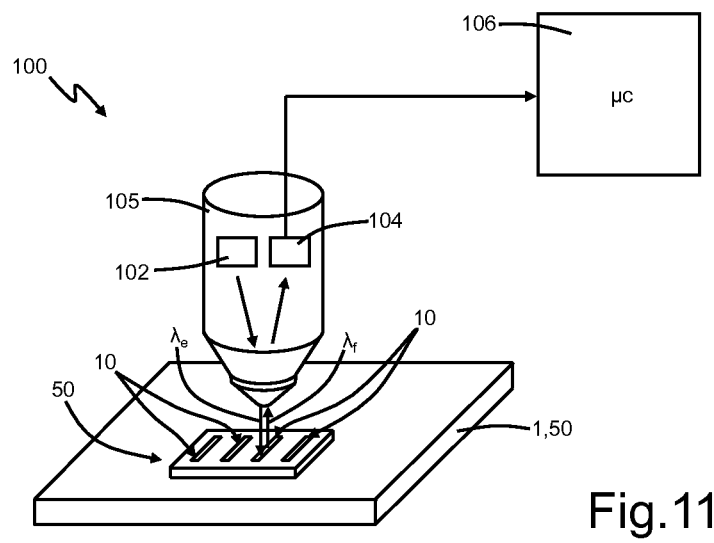
FIG. 11 shows a diagnostic system that uses the diagnostic device of FIG. 1 or FIG. 10.

FIG. 11 shows a diagnostic system 100 that uses the diagnostic device 1 or the diagnostic device 50, or variations thereof.

The diagnostic system 100 comprises a generator of light radiation 102, configured for generating an excitation light radiation having wavelength $\lambda_e$, and a detector 104, configured for collecting an emitted light radiation having wavelength $\lambda_f$ different from the wavelength $\lambda_e$. The generator of light radiation 102 (light source) and the detector 104 belong, according to the representation of FIG. 11, to a fluorescence microscope 105 of a known type (only a portion thereof is represented in the figure), configured for supplying the excitation light radiation to the diagnostic device 1, 50 (in particular to one or more channels 10 thereof), and collecting the possible light radiation emitted by the specific labels present in each channel 10 when they are excited via the excitation light radiation. This is exemplary only, and other light emitting and detecting instrumentation can be employed, as suitable for the assay of interest.

The system 100 can further comprise a processor 106, designed to receive images acquired by the detector 104 and process them in order to identify automatically the intensity of the light radiation emitted by the channel 10 of the diagnostic device 1, or by one or more channels 10 of the diagnostic device 50, and in particular by each of the detection regions 12. It is evident that a diagnosis or conclusion reached on the basis of the value of light intensity detected (for example, higher than a certain minimum threshold, which is considered as noise threshold).

Figure 12:
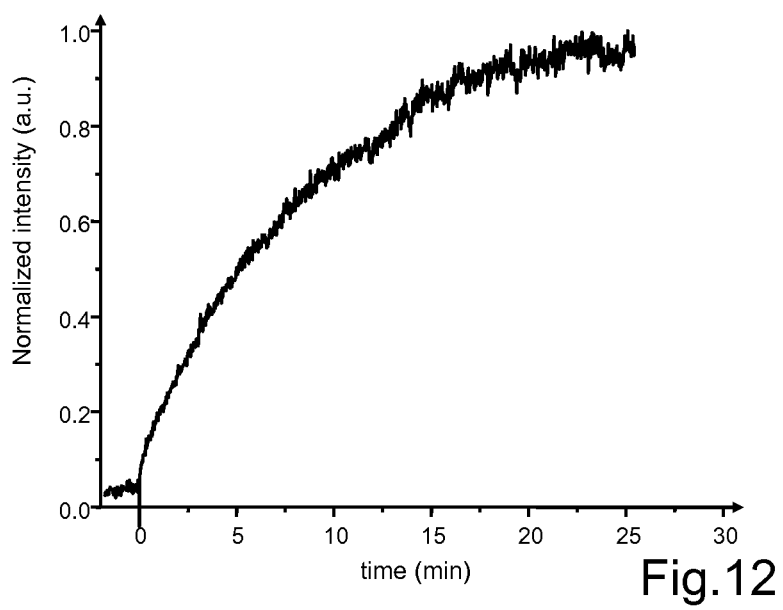
FIG. 12 shows a plot of the light intensity as a function of the time of incubation of fluorescent markers used for carrying out an exemplary diagnosis with the diagnostic device of FIG. 1 or FIG. 10.

FIG. 12 shows by way of example the time variation of the intensity (normalized) of fluorescence during a measurement carried out in real time using the diagnostic device 1. In this case, the detection regions 12 comprise rabbit IgG molecules fixed to the bottom surface 10a of the channel 10, and the target molecules comprise a biological solution of goat anti-rabbit IgG antibodies, marked with fluorochrome Cy3, at a concentration of 1 ng/mL.

The biological solution was made to flow in the channel 10 at a rate of 1 µL/min. In this specific case, the channel 10 had a width of 300 µm and a height of 50 µm. The evolution of the curve of intensity (normalized) of fluorescence as a function of the time of incubation of the biological solution in the channel 10 followed an exponential law until a point of maximum was reached after approximately 20-25 minutes.

The importance of real-time diagnostics is mainly associated with the quantitative aspect of the diagnosis. Carrying out a real-time measurement solves, first of all, problems of non-reproducibility. In addition, it enables drastic reduction of the incubation time.

Finally, in the field of research, real-time analysis enables acquisition of important information on the parameters of kinetics and affinity of the reactions of molecular recognition.

From an examination of the characteristics of the invention provided as disclosed herein the advantages that it affords are evident.

The fluid connections 14 and 16 that enable access to the channel 10 are formed starting from the rear face of the diagnostic device, opposite to the face on which detection of the fluorescence is carried out. This enables a dual advantage; namely, it enables maximization of the active area of the channel 10 and at the same time it affords an advantage in terms of simplicity and low production costs of the diagnostic device, in so far as the channel 10 can be sealed at the top by means of a cover layer 18, for example, of a film or thin-tape type.

The step of sealing of the channel by means of said cover layer 18 does not require thermal procedures or further chemical treatments for favouring sealing.

The use of a thin film or thin tape for sealing the channel 10 at the top moreover makes it possible to conduct the fluorescence analysis via microscope at an extremely short working distance, thus achieving high sensitivity and resolution for real-time detection.

In addition, the use of photoresist for formation of the structural layer 8 enables provision of channels 10 with lateral and vertical dimensions that can be strictly controlled, as well as simplification and economy of the manufacturing process.

In addition, since during all the steps of production the channel 10 is always completely exposed, the steps of cleaning, activation, and functionalization of the channel 10 do not require complicated procedures of manual or mechanical alignment.

Finally, the manufacturing process described is extremely convenient from an economic standpoint, and the diagnostic device can be used with conventional fluorescence microscopes. Other light detecting instrumentation may also be employed, depending on the application.

It is also clear that modifications and variations may be made to the invention described and illustrated herein, without thereby departing from the sphere of protection thereof, as defined in the annexed claims.

For example, we have exemplified the invention with fluorescent labels and a florescent microscope, but the devices can be used with any light generating assays, including fluorescence, phosphorescence (e.g., zinc sulfide, strontium aluminate), chemiluminesence (such as lanthanide materials, phosphorous, luminol) and bioluminescence (such as green fluorescent protein (GFP) or luciferase) and the instrumentation appropriate thereto.

As another example of variation, only one of the inlet and outlet holes 14, 16 may be present. In this case, the single hole present has both the function access to the channel for filling the latter and the function of emptying out the channel. Alternatively, if the device is intended to be a single use disposable device, no emptying function may be required.

In addition, in the case of a multichannel diagnostic device 50, each channel can be functionalized in a way different from other channels, in such a way as to enable a plurality of different diagnoses or assays using one and the same diagnostic device 50.

In addition, as an alternative to the fluorescence technique described, the diagnostic step can be carried out using quantitative spectroscopic techniques, such as, for example, X-ray photoelectron spectroscopy (XPS) and/or attenuated total reflection (ATR) spectroscopy, and the like. In the latter case, it may be expedient for the diagnostics to be carried out with the channel 10 completely emptied and with the diagnostic device 1 without the cover layer 18 (the cover layer 18 is, for example, removed immediately after the period of incubation of the liquid to be analysed in the channel 10, before the diagnostic step).

Figure 3:
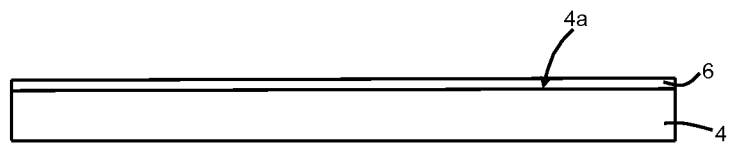
FIGS. 3-9 show, in cross-sectional view along the line II-II of FIG. 1, successive steps of a method for manufacturing the device of FIGS. 1 and 2.

Finally, the step of etching of the substrate 4 and of the compatible layer 6 to form the inlet hole 14 and outlet hole 16 (as described with reference to FIG. 6) can be carried out prior to formation of the layer 41, for example, immediately following upon the step of formation of the compatible layer 6 (i.e., immediately after the steps described with reference to FIG. 3). Alternatively, in the case where the compatible layer 6 is grown on the substrate 4, it is sufficient to carry out a single etching step of just the substrate 4 prior to the step of growth of the compatible layer 6, and only after growth of the compatible layer 6. The process of growth occurs not only on the surface of the substrate 4, but also on the walls of the holes just formed. In this way, there is obtained a maximum compatibility of the inlet hole 14 and outlet hole 16 even in the case where the substrate 4 is not perfectly compatible with the chosen assay.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

What is claimed is:

1. A microfluidic diagnostic device comprising:
a substrate;
a compatible layer formed on a upper face of the substrate and having a refraction index;
a structural layer, formed on top of the compatible layer;
a channel, formed in the structural layer and limited underneath by the compatible layer, said channel being optically accessible from above by a first luminous radiation having a first wavelength ($\lambda_e$); and
an inlet hole and an outlet hole each extending through the substrate and the compatible layer and in microfluidic connection with said channel, said inlet hole and said outlet hole formed starting from a bottom, external face of said microfluidic diagnostic device, opposite to an optically accessible top face,
said compatible layer being substantially transparent to the first wavelength ($\lambda_e$) and having a thickness equal to approximately a quarter of the first wavelength ($\lambda_e$) divided by the refraction index of said compatible layer, or equal to an odd multiple of a quarter of the first wavelength ($\lambda_e$) divided by the refraction index of said compatible layer; and
the compatible layer being arranged in such a way that the incidence angle of the incident light radiation is approximately orthogonal to the surface of the compatible layer.

2. The device according to claim 1, wherein said substrate is made of silicon, and the compatible layer is made of silicon oxide.

3. The device according to claim 1, further comprising a cover layer made of a material transparent to the first wavelength ($\lambda_e$), arranged on top of the structural layer and sealing the channel at the top.

4. The device according to claim 3, wherein the cover layer is made of a polymeric material transparent to said first wavelength ($\lambda_e$).

5. The device according to claim 2, wherein the structural layer is made of photoresist.

6. The device according to claim 1, wherein said channel has a shape chosen in the group comprising rectangular, circular, polygonal, and polygonal with rounded corners, and extends in depth in the structural layer throughout the thickness of the structural layer.

7. The device according to claim 1, wherein said channel has a height of between 1 μm and 1000 μm.

8. The device according to claim 1, further comprising a supporting layer, formed on a second face, opposite to the first face, of the substrate and comprising a through hole arranged as a continuation of the inlet hole, said through hole being provided with a removable hermetic closing element.

9. The device according to claim 1, wherein said channel houses at least one detection region comprising probe molecules adapted to detect respective target molecules.

10. The device according to claim 9, wherein said probe molecules are grafted to the compatible layer inside the channel.

11. The device according to claim 10, wherein said probe molecules are labelled with marker molecules which, when activated and excited by said first luminous radiation, are adapted to emit a second luminous radiation having a second wavelength ($\lambda_f$), said compatible layer being transparent to said first and said second luminous radiation.

12. A diagnostic system comprising:
a microfluidic diagnostic device according to claim 3;
a generator of light radiation facing the cover layer and configured for generating excitation light radiation having the first wavelength ($\lambda_e$) towards said microfluidic diagnostic device;
a detector of light radiation facing the cover layer and configured for collecting a light radiation emitted by said microfluidic diagnostic device, said emitted light radiation having a second wavelength ($\lambda_f$) different from the first wavelength ($\lambda_e$); and
a processor, connected to the detector of light radiation and configured for acquiring an image of said emitted light radiation and identifying, from said image, an intensity of said emitted light radiation.

13. The system according to claim 12, comprising a fluorescence microscope including the generator of light radiation and the detector of light radiation.

* * * * *